United States Patent
Savall et al.

(10) Patent No.: US 11,504,200 B2
(45) Date of Patent: Nov. 22, 2022

(54) WEARABLE USER INTERFACE DEVICE

(71) Applicant: Verb Surgical Inc., Mountain View, CA (US)

(72) Inventors: Joan Savall, Palo Alto, CA (US); Richard Edward DeMartini, San Mateo, CA (US); Randall Blake Hellman, San Francisco, CA (US); Denise Ann Miller, Scotts Valley, CA (US); Anette Lia Freiin von Kapri, Mountain View, CA (US); Pablo E. Garcia Kilroy, Menlo Park, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 893 days.

(21) Appl. No.: 16/256,888

(22) Filed: Jan. 24, 2019

(65) Prior Publication Data

US 2020/0237467 A1 Jul. 30, 2020

(51) Int. Cl.
*A61B 34/00* (2016.01)
*G06F 3/01* (2006.01)
(Continued)

(52) U.S. Cl.
CPC .............. *A61B 34/74* (2016.02); *A61B 34/25* (2016.02); *A61B 34/30* (2016.02); *B25J 13/02* (2013.01);
(Continued)

(58) Field of Classification Search
CPC ......... A61B 34/74; A61B 34/25; A61B 34/30; A61B 2034/741; A61B 2034/2048;
(Continued)

(56) References Cited

U.S. PATENT DOCUMENTS

| 2001/0034947 A1 | 11/2001 | Nagata |
| 2003/0023346 A1 | 1/2003 | Salisbury, Jr. et al. |

(Continued)

FOREIGN PATENT DOCUMENTS

| EP | 2671686 B1 | 5/2016 |
| WO | 2017031132 A1 | 2/2017 |

(Continued)

OTHER PUBLICATIONS

International Search Report and Written Opinion for International Application No. PCT/US2019/060966, dated Apr. 9, 2020, 12 pages.

(Continued)

*Primary Examiner* — Phuong H Nguyen (74) *Attorney, Agent, or Firm* — Womble Bond Dickinson (US) LLP (57) ABSTRACT

Wearable user interface devices are described. A wearable user interface device can include a wearable base connected to a trackable device component by a linkage. The linkage can connect to a pivoted support that the trackable device is mounted on, and which maintains poses when the user interface device is not manipulated by a user's hand. The pivoted support has several orthogonal axes intersecting at a center of rotation located inside a device body of the trackable device. Other embodiments are also described and claimed.

20 Claims, 6 Drawing Sheets

(51) Int. Cl.
*A61B 34/30* (2016.01)
*B25J 13/02* (2006.01)
*G05G 1/04* (2006.01)

(52) U.S. Cl.
CPC .............. *G05G 1/04* (2013.01); *G06F 3/014* (2013.01); *G06F 3/017* (2013.01); *A61B 2034/741* (2016.02)

(58) Field of Classification Search
CPC ..... A61B 2034/2051; A61B 2034/2059; B25J 13/02; G05G 1/04; G06F 3/014; G06F 3/017
See application file for complete search history.

(56) References Cited

U.S. PATENT DOCUMENTS

| | | |
|---|---|---|
| 2008/0103492 A1 | 5/2008 | Morley et al. |
| 2011/0118748 A1* | 5/2011 | Itkowitz ................. A61B 34/30 606/130 |
| 2013/0025055 A1 | 1/2013 | Saracen et al. |
| 2014/0018960 A1 | 1/2014 | Itkowitz |
| 2017/0189128 A1* | 7/2017 | Auld ....................... A61B 34/30 |
| 2018/0161108 A1 | 6/2018 | Savaii et al. |
| 2018/0168759 A1* | 6/2018 | Kilroy ................... B25J 13/025 |

FOREIGN PATENT DOCUMENTS

| | | |
|---|---|---|
| WO | 2018107062 A1 | 6/2018 |
| WO | 2018154559 A1 | 8/2018 |

OTHER PUBLICATIONS

International Preliminary Report on Patentability from related International Application No. PCT/US2019/060966, dated Aug. 5, 2021, 6 pages.

Extended European Search Report from related European Application No. 19911375.4 dated Sep. 19, 2022 (9 pages).

* cited by examiner

WEARABLE USER INTERFACE DEVICE

BACKGROUND

Field

Embodiments related to user interface devices are disclosed. More particularly, embodiments related to wearable user interface devices are disclosed.

Background Information

Endoscopic surgery involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted tools.

A surgical robotic system may be remotely operated by a surgeon to control a robotically-assisted tool located at an operating table. The surgeon may use a computer console located in the operating room, or it may be located in a different city, to command a robot to manipulate the surgical tool mounted on the operating table. The robotically-controlled surgical tool can be a grasper mounted on a robotic arm. Accordingly, the surgical robotic system may be controlled by the remote surgeon to grasp tissue during a robotic surgery.

Control of the surgical robotic system may require control inputs from the surgeon. For example, the surgeon may hold in her hand a user input device such as a joystick or a computer mouse that she manipulates to generate the signals for the control commands that control motion of the surgical robotic system components, e.g., an actuator, a robotic arm, and/or a surgical tool of the robotic system.

SUMMARY

Existing user input devices include hand controllers used to command a surgical robotic system. The hand controllers may include a grip that is supported by a linkage system having at least four degrees of freedom. The four degrees of freedom are required to avoid singularities in the movement of the grip. A singularity occurs when axes of the degrees of freedom align with each other, and cause the linkage system to bind. When the linkage system binds, movement of the hand controller is disrupted. In addition to being complex, the linkage system of existing hand controllers do not allow for precise finger manipulation or a natural feel when manipulating the grip. As a result, a dexterity and precision of movements commanded by existing hand controllers may be limited, and the existing hand controllers may cause user fatigue or control errors.

A user interface device (UID) for manipulating a surgical instrument in a surgical robotic system is provided. The UID is wearable on a user's hand. The UID includes a trackable device body that is on a center of rotation of a pivoted support that connects to a wearable base. The UID maintains the center of rotation within a range of the user's hand motion, and thus, a likelihood of a singularity in the movement of the device body is reduced. Accordingly, the UID provides high dexterity and a natural feel to the user.

In an embodiment, the UID includes a wearable base that can be worn on a user's hand The UID includes a linkage having a first end mounted on the wearable base, and a second end coupled to a pivoted support. A device body of the UID can be mounted on the pivoted support such that three orthogonal axes of the pivoted support intersect a center of rotation located inside of the device body. The UID can include one or more tracking sensors within the device body for tracking movements of the UID. The tracked movements can be used to control motions of a surgical instrument in a surgical robotic system. For example, the surgical robotic system can include the surgical instrument mounted on a surgical robotic arm, and one or more processors of the surgical robotic system can be configured to control motions of the surgical instrument based on the tracked movements of the UID.

In an embodiment, the center of rotation is positioned at the fingertips of the user's hand The second end of the linkage can extend from the first end of the linkage, and one or more support members can be coupled to each other via joints to provide one or more degrees of freedom of translation between the first end and the second end. The linkage can include a pivoted support having one or more of a roll suspension, a pitch suspension, or a yaw suspension, and the suspensions can be interconnected by joints. The pivoted support having the movable suspensions can be coupled to the second end of the linkage having the movable support members. Accordingly, the linkage and the pivoted support components can allow for movement of the center of rotation with movements of the user's hand when the user is holding the UID. The movement of the center of rotation allows the user to rotate the user's hand directly around the center of rotation that remains positioned at the fingertips. Furthermore, the joints of the linkage and the pivoted support can maintain a pose of the UID, e.g., relative to the center of rotation, when the UID is not being touched or manipulated by the user's hand or fingers.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Embodiments of a wearable user interface device (UID) for providing command signals are described below. The command signals can be used to control a robotic system. The robotic system can be a surgical robotic system. The UID signals may, however, be used to control other systems, such as interventional cardiology systems, vision systems, or aircraft systems, to name only a few possible applications.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction away from a reference point, e.g., away from a hand of a user. Similarly, "proximal" may indicate a location in a second direction opposite to the first direction, e.g., toward the hand of the user. Such terms are provided to establish relative frames of reference, however, and are not intended to limit the use or orientation of a UID to a specific configuration described in the various embodiments below.

In an aspect, a UID for providing command signals can be worn on a user's hand. The UID includes a wearable base that can connect to a linkage and/or a pivoted support on which a trackable device component is mounted. The pivoted support can have three orthogonal axes intersecting at a center of rotation located inside a device body of the device component. Accordingly, the UID can be worn and manipulated by the user's hand by moving the device body about the center of rotation to provide highly dexterous and precise control. More particularly, the UID can allow the user to rotate the UID around its own axis of rotation, and thus, the user can have improved control over UID movements. The command signals from the UID can be used for manipulating a surgical instrument in a surgical robotic system. Such application is provided by way of example in the description below, however, and it will be appreciated that the UID can be used in any application that links the transformation of the UID to a transformation of a physical or virtual object that is being controlled. Control of the surgical instrument is therefore provided as a non-limiting example of an object that the UID-provided command signals can be used to control.

In the surgical robotic system use case, the surgical robotic system can be a robotic-assisted surgical system that is a software-controlled, electromechanical system designed for surgeons to perform minimally-invasive surgery. The surgical robotic system can be used with an endoscope, compatible endoscopic instruments, and accessories. The system may be used by trained physicians tin an operating room environment to assist in the accurate control of compatible endoscopic instruments during robotically-assisted urologic, gynecologic, and other laparoscopic surgical procedures. The compatible endoscopic instruments and accessories for use with the surgical robotic system are intended for endoscopic manipulation of tissue including grasping, cutting, blunt, and sharp dissection, approximation, ligation, electrocautery, and suturing.

Figure 1:
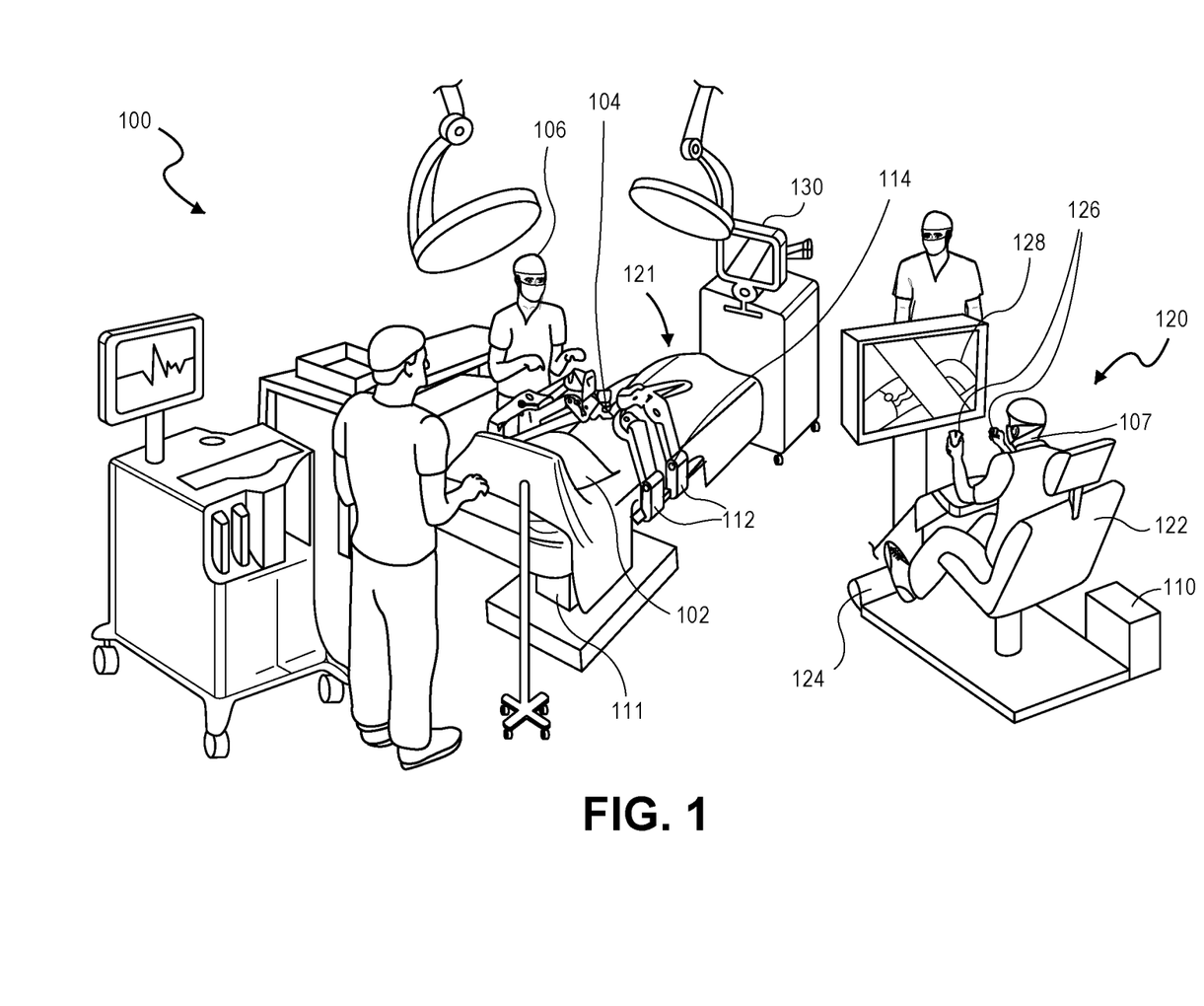
FIG. 1 is a pictorial view of an example surgical robotic system in an operating arena, in accordance with an embodiment.

Referring to FIG. 1, this is a pictorial view of an example surgical robotic system 100 in an operating arena. The surgical robotic system 100 includes a user console 120, a control tower 130, and a surgical robot 121 having one or more surgical robotic arms 112 mounted on a surgical platform 111, e.g., a table, a bed, etc. The surgical robotic system 100 can incorporate any number of devices, tools, or accessories used to perform surgery on a patient 102. For example, the surgical robotic system 100 may include one or more surgical instruments (or "tools") 104 used to perform surgery. A surgical instrument 104 may have an end effector that is mounted on or attached to a distal end of a surgical robotic arm 112, for executing a surgical procedure.

Each surgical instrument 104 may be manipulated manually, robotically, or both, during the surgery. For example, surgical instrument 104 may be a tool used to enter, view, or manipulate an internal anatomy of patient 102. In an embodiment, surgical instrument 104 is a grasper that can grasp tissue of patient 102. Surgical instrument 104 may be handled manually, by a user 106; or it may be manipulated robotically, via actuated movement of the surgical robotic arm 112 to which it is attached. Surgical robotic arms 112 are shown as a table-mounted system, but in other configurations the surgical robotic arms 112 may be mounted in a cart, ceiling or sidewall, or in another suitable structural support.

Generally, a user 107, such as a surgeon or other operator (user), may use the user console 120 to remotely manipulate the surgical robotic arms 112 and/or surgical instruments 104, e.g., by teleoperation. The user console 120 may be located in the same operating room as the surgical robot 121, as shown in FIG. 1. In other environments however, the user console 120 may be located in an adjacent or nearby room, or it may be at a remote location, e.g., in a different building, city, or country. The user console 120 may comprise a seat 122, pedals 124, one or more handheld user interface devices (UIDS) 126, and an open display 128 that is configured to display, for example, a view of the surgical site inside patient 102. As shown in the exemplary user console 120, a surgeon 107 sitting in seat 122 and viewing the open display 128 may manipulate pedals 124 and/or handheld UID 126 to remotely control the surgical robotic arms 112 and/or surgical instruments 104 mounted to the distal ends of the surgical robotic arms 112. Pedals 124 can be foot pedals, such as seven pedals, that generate motion control signals when actuated. User console 120 may include one or more additional interface devices, such as a keyboard or a joystick, to receive manual inputs to command operations of surgical robotic system 100.

In some variations, user 106 may also operate surgical robotic system 100 in an "over the bed" (OTB) mode, in which the user 106 is at a side of patient 102 and is simultaneously manipulating a robotically-driven tool/end effector attached thereto. For example, the user's left hand may be manipulating a handheld UID 126 to control a robotic component, while the user's right hand may be manipulating a manual laparoscopic tool. Thus, in these variations, the user may perform both robotic-assisted minimally invasive surgery (MIS) and manual laparoscopic surgery on patient 102.

During an exemplary procedure or surgery, patient 102 is prepped and draped in a sterile fashion to achieve anesthesia. Initial access to the surgical site may be performed manually with the surgical robotic system 100 in a stowed configuration or withdrawn configuration to facilitate access to the surgical site. Once access is completed, initial positioning and/or preparation of the surgical robotic system 100 may be performed. During the procedure, a surgeon 107 in the user console 120 may utilize the pedals 124 and/or UIDs 122 to manipulate various end effectors and/or imaging systems to perform the surgery. Manual assistance may also be provided at the procedure table by sterile-gowned personnel, e.g., user 106, who may perform tasks including but not limited to, retracting tissues or performing manual repositioning or tool exchange involving one or more surgical robotic arms 112. Non-sterile personnel may also be present to assist surgeon 107 at the user console 120. When the procedure or surgery is completed, the surgical robotic system 100 and/or user console 120 may be configured or set in a state to facilitate post-operative procedures, including but not limited to, surgical robotic system 100 cleaning and/or sterilization, and/or healthcare record entry or printout, whether electronic or hard copy, such as via user console 120.

In one embodiment, surgeon 107 holds and moves UID 126 to provide an input command to move a robot arm actuator 114 in surgical robotic system 100. UID 126 may be communicatively coupled to the rest of surgical robotic system 100, e.g., via a console computer system 110. UID 126 can generate spatial state signals corresponding to movement of UID 126, e.g., position and orientation of the handheld housing of the UID, and the spatial state signals may be input signals used to control a motion of the surgical robotic arm 112 or a tool drive loaded with a surgical instrument 104. For example, the tracking sensor of UID 126 can generate an input pose signal for controlling spatial motion of a corresponding surgical tool 104. Surgical robotic system 100 may use control signals derived from the spatial state signals, to control proportional motion of actuator 114. In one embodiment, one or more processors, e.g., a console processor of console computer system 110 receives the spatial state signals and generates the corresponding control signals. Based on these control signals, which control how the actuator 114 is energized to move a segment or link of surgical robotic arm 112, the movement of a corresponding surgical tool that is attached to the arm may mimic the movement of UID 126. Similarly, interaction between surgeon 107 and UID 126 can generate for example a grip control signal that causes a jaw of a grasper of the surgical tool to close and grip the tissue of patient 102. For example, the one or more processors can be configured to control the surgical tools based on at least one of the input pose signal and a grip signal, as described below.

Surgical robotic system 100 may include several UIDs 126, where respective control signals are generated for each UID that control the actuators of a respective surgical robotic arm 112 or a surgical tool (end effector). For example, surgeon 107 may move a first UID 126 to command the motion of actuator 114 that is in a left surgical robotic arm, where the actuator responds by moving linkages, gears, etc., in that surgical robotic arm 112. Similarly, movement of a second UID 126 by surgeon 107 commands the motion of another actuator 114, which in turn moves other linkages, gears, etc., of the surgical robotic system 100. Surgical robotic system 100 may include a right surgical robotic arm 112 that is secured to the bed or table to the right side of the patient, and a left surgical robotic arm 112 that is at the left side of the patient. An actuator 114 may include one or more motors that are controlled so that they drive the rotation of a joint of surgical robotic arm 112, to for example change, relative to the patient, an orientation of an endoscope or a grasper of the surgical tool that is attached to that arm. Motion of several actuators 114 in the same surgical robotic arm 112 can be controlled by the spatial state signals generated from a particular UID 126. UIDs 126 can also command motion of respective surgical tools. For example, each UID 126 can generate a respective grip signal to control motion of an actuator, e.g., a linear actuator, that opens or closes jaws of a grasper at a distal end of the surgical tool to grip tissue within patient 102.

In some aspects, the communication between surgical robot 121 and user console 120 may be through a control tower 130, which may translate user commands that are received from user console 120 to robotic control commands and transmit the control commands to the surgical robot 121. The control tower 130 may also transmit status and feedback from surgical robot 121 back to user console 120. The connections between the surgical robot 121, user console 120, and control tower 130 may be via wired and/or wireless connections, and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic healthcare record system.

It will be appreciated that the operating room scene in FIG. 1 is illustrative and may not accurately represent certain medical practices.

Figure 2:
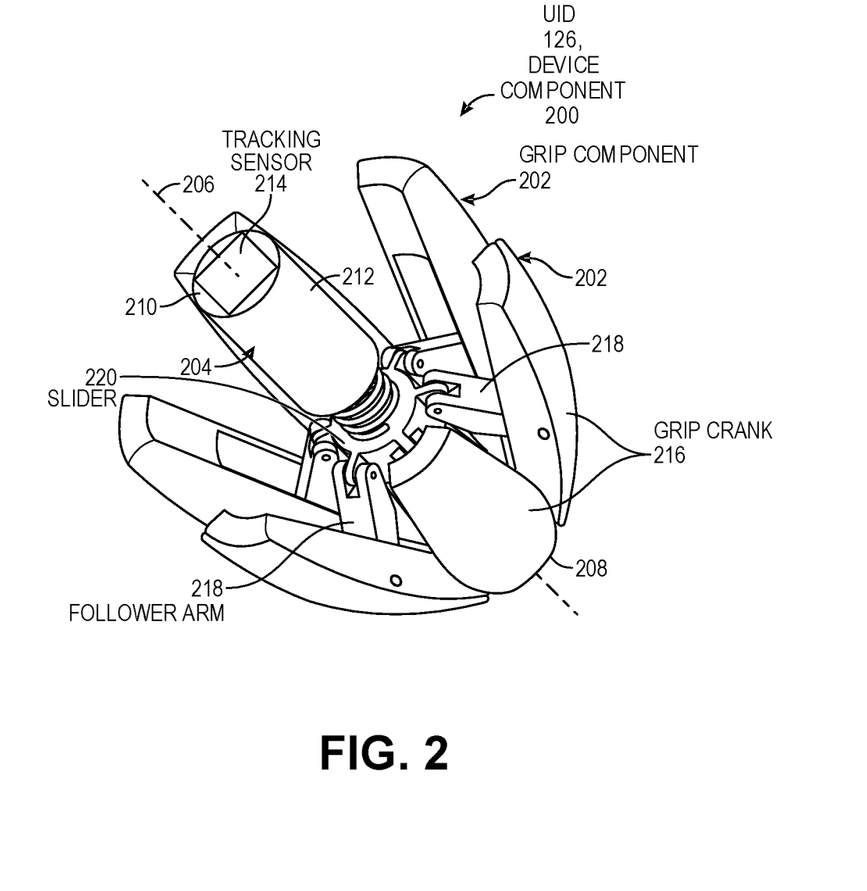
FIG. 2 is a perspective view of a device component of a wearable user interface device, in accordance with an embodiment.

Referring to FIG. 2, a perspective view of a device component of a wearable user interface device is shown in accordance with an embodiment. A UID 126 can be used by a user for manipulating surgical instrument 104 in surgical robotic system 100. UID 126 can include a device component 200 to be held by a user, e.g., surgeon 107. For example, the device component 200 may include several grip components 202 extending outward from a centrally located device body 204. The user may hold portions of the grip components 202 between several fingers and move the device component 200 within a workspace. The workspace may be a range of reach of the user.

In an embodiment, device body 204 extends in a longitudinal direction along a central axis 206. For example, device body 204 may extend longitudinally from a proximal end 208 that is normally cupped within a hand of surgeon 107 when the user is holding the grip components 202. Device body 204 may extend to a distal end 210 having a forward-facing surface. Device body 204 can be segmented into several portions. A distal portion of device body 204 may include a device head 212 having an outer surface extending around central axis 206. The outer surface of device head 212 can be cylindrical, and may surround a cavity, lumen, or other internal volume configured to receive electronics and/or other components. For example, the internal volume may include at least a printed circuit board (PCB). Alternatively, the PCB can be located external to the device body 204, and placed in communication with other electronics contained in the internal volume. The PCB and/or other electronics of UID 126 can be powered by an internal or external power source. For example, a battery may be contained in the internal volume for powering the PCB and other electrical components in the UID 126. Alternatively, as described below, a power cable (e.g., a USB interface wire) can deliver power to UID 126 from an external power supply. Power can also be transmitted to UID 126 wirelessly, e.g., via inductive coupling, or any other power transfer modality. Accordingly, Furthermore, one or more tracking sensors 214, such as accelerometers, gyroscopes, magnetometers, and/or other optical, magnetic, or capacitive sensors can be disposed inside or on an outer surface of UID 126. For example, the cavity within device head 212 can receive one or more tracking sensors 214 used to track movement of UID 126. More particularly, a tracking sensor 214 may be mounted within device body 204 for tracking positions and orientations of UID 126 in six degrees of freedom. Tracking sensor 214 can be fixed to device head 212, and thus, tracking sensor 214 may experience the same movement as device head 212. Accordingly, tracking sensor 214 can be used for tracking movements of the UID, and the tracked movements can be used to control motions of surgical instrument 104.

Tracking sensor 214 can be configured to generate an input spatial state signal to control motion of the surgical instrument 104. The input spatial state signal can be generated in response to movement of device body 204. Tracking sensor 214 can detect a position and/or orientation of device body 204 when surgeon 107 moves UID 126, and the detected position and/or orientation may be correlated to a control of a surgical robotic system 100. For example, tracking sensor 214 may detect motion in several degrees of freedom, e.g., translation in one or more directions, rotation about one or more axes, or tilting relative to one or more axes, of device body 204 within the workspace. The tracking sensor 214 may include one or more of an accelerometer, a gyroscope, another inertial sensor, a six-degree-of-freedom position sensor, e.g., an electromagnetic tracking sensor including components, e.g., coils, having a parameter responsive to a surrounding magnetic field and measurable, e.g., by a tracking system, to determine a position or orientation of the sensor. Such tracking sensor embodiments are provided by way of example and not limitation.

User console 120 may include UID 126 as a component for manipulating surgical instrument 104 in surgical robotic system 100. In an embodiment, user console 120 can incorporate a tracking system to track movements, e.g., the positions and orientations, of UID 126. For example, user console 120 may be connected to tracking sensor 214 by a wired or wireless link, and the tracking system of user console 120 can be configured to track movements of UID 126 based on signals received through the link to generate signals to control motions of surgical instrument 104. In some variations, the tracking system may use optical tracking, in which cameras may be mounted in front of the user to capture continuous images of the UID movement. One or more markers can be printed or mounted on the UID 126 so that images can be processed to detect positions and orientations of the UID 126. In other variations, the camera can be mounted on the UID 126. Alternatively or in addition, the tracking system may be based on electromagnetic tracking subsystem having an electromagnetic source. Magnetic tracking can determine the position/orientation of moveable sensors relative to a fixed transmitter within a defined operating space. The sensors precisely measure the magnetic field from a transmitter, which is configured to generate a known set of field patterns. The transmitted patterns are arranged such that the system can resolve a unique spatial position and orientation from the values measured by each sensor. For example, the user console 110 may have a field generator to generate a position-varying magnetic field to establish a coordinate space in front of the user, while the UID 126 may include one or more tracking sensors capable of measuring six degrees of freedom within the coordinate space. The tracking sensors may include coils that respond to the electromagnetic field, e.g., inducing current. By measuring the coil current, a position and orientation of the tracking sensor and the UID 116 can be determined.

The tracked spatial state information can then be forwarded by the user console 120 to the control tower 130 as user input for robotic control. A control computer at the control tower 130 can process the user input to generate control commands so that end effectors of the surgical instrument or tool closely follow the tracked movements of the UID 116, which includes translations and rotations along all three axes, i.e., 6 DOF, in space. In addition to the spatial state, other gestures such as a squeeze or grip may also be tracked by one or more sensors, which can be a proximity sensor detecting deformation or mechanical linkages being pressed by user fingers, as described below. Once detected, the UID 126 may generate a grip signal and transmit the grip signal to the user console. The signals can be input to the control tower 130 for generating tool control commands such as grasping. For example, a grip signal may be translated into a tool control command to close the jaws of a grasper, while a release signal may be mapped to an open jaw command. Furthermore, the grip signal may command the surgical tool to apply grip force on tissues or surgical devices.

UID 126, which is handled by surgeon 107 to command surgical instrument 104 and/or surgical robotic arms 112, can be ergonomic. For example, UID 126 can include several, e.g., at least three, grip components 202 extending radially outward from central axis 206 at angles to one another. Accordingly, surgeon 107 can comfortably hold grip components 202 between an extended thumb, index finger, and middle finger. Each grip component 202 can include a grip linkage, which may include a grip crank 216 having an exterior gripping surface to be pressed by a finger of surgeon 107. The grip components 202 can be pivotally coupled to device body 204 at a corresponding pivot such that pressure applied to grip crank 216 by the finger of surgeon 107 can move grip crank 216 radially inward toward device body 204. For example, grip components 202 can be connected to device body 204 near a proximal end 208.

Movement of the grip cranks 216 can cause movement of other components of grip components 202. Each grip component 202 can be a slider-crank mechanism, and the grip components 202 can have grounds (pivots of grip cranks 216) that are linked to device body 204. Each grip component 202 can include a follower arm 218 pivotally coupled to grip crank 216 at a corresponding pivot. Furthermore, follower arm 218 can extend radially inward from grip crank 216 to a slider 220. Follower arm 218 can be pivotally coupled to slider 220 at a corresponding pivot joint. Whereas grip cranks 216 may be grounded to device body 204 at pivot joints, slider 220 may be slidably coupled to device body 204.

UID 126 optionally includes a finger clutch, such as touch sensors or mechanical switches, to temporarily clutch the surgical robot. When clutched, the surgical robot 121 may pause the movement of one or more of the tool or arm actuators in response to the clutch signal. The teleoperation can be put on hold regardless of any UID movements, i.e., spatial state and/or grip signals are ignored by the system. During the clutch period, the user can repositions UID(s) 126, for example, to the center of a tracking field, without causing unwanted movement of surgical robot 121 or surgical tools 104. Similarly, the user may squeeze (or release) the grip cranks 216 without changing a jaw angle or gripping force of a grasper.

UID 126 can be held in a user's hand and manipulated by the fingertips of the hand That is, the user's hand can rotate, roll, or twist UID 126 to precisely maneuver surgical instrument 104. There is a risk, however, when manipulating an ungrounded (not mounted on a surface of the operating room) UID 126 in free space, that the user may accidentally drop UID 126. Accordingly, the ungrounded UID 126 may be wearable such that device body 204 is suspended in space even when the user is not holding the device component 200.

Figure 3:
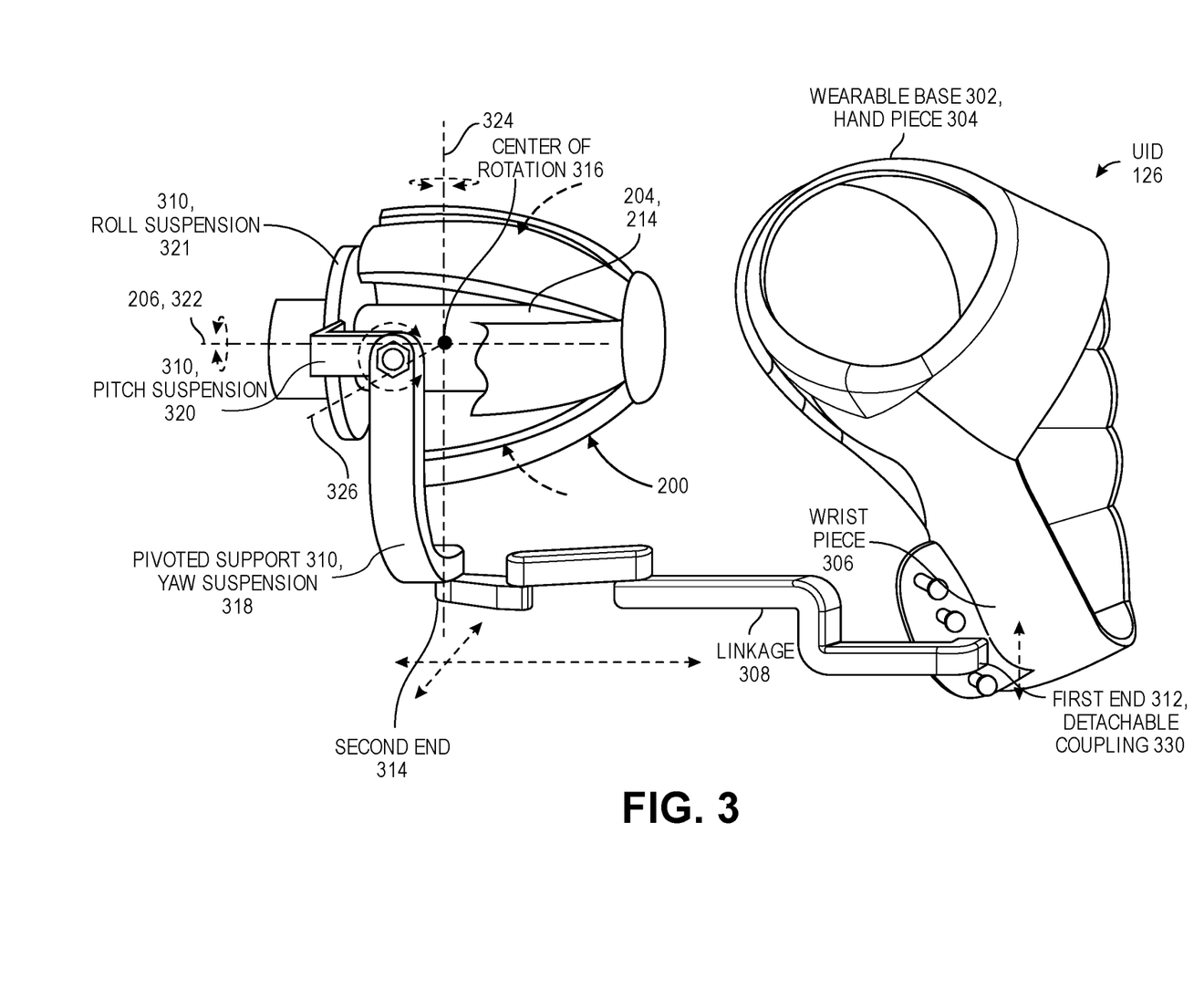
FIG. 3 is a side view of a wearable user interface device, in accordance with an embodiment.

Referring to FIG. 3, a side view of a wearable user interface device is shown in accordance with an embodiment. UID 126 can include a wearable base 302 that can be worn on a user's hand. Wearable base 302 can be a band, a fixture, a glove, or another wearable component that can be hand-worn and may be user-adjustable. Wearable base 302 may include a hand piece 304 to be worn on or around the user's hand. The hand piece 304 can have a loop or a c-shaped member that fits over a portion of the hand or fingers, such as around a thumb of the user. In an embodiment, the c-shaped member is a clip component that clamps onto the back of the hand and the palm of the hand. Wearable base 302 can include a wrist piece 306 to be worn on or around a wrist of the user. For example, wearable base 302 may include a strap, a loop, or a c-shaped member that can securely fit on the wrist of the user.

When the wearable base 302 is mounted on the user's hand, the hand is established as a ground reference for UID 126. For example, the user can slip her hand into the wearable part of wearable base 302 and grab the device component 200 of UID 126 with her fingers. As described below, the device component 200 can be connected to wearable base 302 by a support structure, and thus, wearable base 302 effectively acts as a ground link such that UID 126 is an ungrounded control device that is nonetheless anchored (to the user).

The hand attachment of wearable base 302 can be adjustable. For example, hand piece 304 or wrist piece 306 can include a flexible band that resiliently fits to the user's hand. Similarly, hand attachment can include a custom-fit molded material, e.g., a molded band that conforms to the shape of the user's hand. The band, strap, loop, etc., of wearable base 302 can be adjusted to be tighter or looser to fit the user's hand size.

The support structure that connects the device component 200 to wearable base 302 can include a linkage 308 and a pivoted support 310. Linkage 308 can include a first end 312 mounted on wearable base 302. The linkage 308 can extend from first end 312 to a second end 314. Linkage 308 can be referred to as a planar mechanism because, as described further below, linkage 308 can articulate such that second end 314 moves relative to first end 312 along a plane. More particularly, second end 314 can move along one or more planes, e.g., within an x-y plane, an x-z plane, or a y-z plane to adjust a relative direction and distance between the linkage ends. For example, second end 314 can translate in several directions, e.g., along several orthogonal axes, relative to first end 312 that is anchored to wearable base 302. The several orthogonal axes may be within a same plane, e.g., a horizontal plane, and thus, the planar mechanism can provide two degrees of freedom of translation between first end 312 and second end 314. When the orthogonal axes are in several planes, the linkage 308 provides three degrees of freedom of translation.

Pivoted support 310 can be connected to second end 314 of linkage 308. For example, pivoted support 310 can include a yaw suspension 318 that is mounted on linkage 308 at second end 314. Similarly, a pitch suspension 320 can be mounted on yaw suspension 318. In an embodiment, the device component 200 is mounted on pitch suspension 320. For example, pivoted support 310 may include a roll suspension 321 that is connected to an end of pitch suspension 320, and device body 204 may be supported by roll suspension 321. In an embodiment, roll suspension 321 is a collar that extends around device body 204 and central axis 206. For example, the collar can be distal of a center of rotation 316, e.g., on an opposite side of center of rotation 316 from wearable base 302, to support a front end of device body 204. Accordingly, device body 204 can be connected to linkage 308 and wearable base 302 through one or more suspensions of pivoted support 310.

Each suspension of pivoted support 310 can have a respective axis. For example, roll suspension 321 can have a roll axis 322 extending through device body 204, e.g., collinear or parallel to central axis 206. Yaw suspension 318 can have a yaw axis 324 extending through a joint connecting yaw suspension 318 to linkage 308 at second end 314. Similarly, pitch suspension 320 can have a pitch axis 326 extending through a joint connecting pitch suspension 320 to yaw suspension 318. In an embodiment, the suspension axes of pivoted support 310 intersect at center of rotation 316. For example, roll axis 322, yaw axis 324, and pitch axis 326 can intersect at center of rotation 316. Furthermore, the intersecting axes may be orthogonal to each other. For example, roll axis 322, pitch axis 326, and yaw axis 324 may be orthogonal to each other at center of rotation 316. Accordingly, pivoted support 310 can have three orthogonal axes intersecting at center of rotation 316.

Center of rotation 316 of pivoted support 310 can be located inside device body 204. Accordingly one or more sensors of device body can be positioned on center of rotation 316. For example, tracking sensor 214 within the device body 204 may be positioned on center of rotation 316. Center of rotation 316 can be located within the envelope of grip components 202. For example, device body 204 may be radially inward from grip components 202 relative to central axis 206, and thus, center of rotation 316, which is located within (radially inward of) an outer surface of device body 204, may also be located within a spatial envelope defined by the outer surfaces of grip components 202.

In an embodiment, linkage 308 and/or pivoted support 310 are detachable from wearable base 302. For example, linkage 308 can include a detachable coupling 330 at first end 312. Detachable coupling 330 may be a socket that connects to one or more ball-tipped prongs on wearable base 302. For example, the prongs can be arranged vertically along wrist piece 306 of wearable base 302. Detachable coupling 330 may connect to each prong by a snap fit. The socket of detachable coupling 330 can be pulled off of a first prong and pressed onto a second prong to change the location of first end 312 at wearable base 302. A user with relatively large hands may lower first end 312 such that center of rotation 316 is positioned at a comfortable location. Accordingly, linkage 308 can be attached to wearable base 302 at several locations based on a preference of the user.

Linkage 308 can be attached to wearable base 302 at locations other than those illustrated in FIG. 3. More particularly, although linkage 308 is shown having first end 312 at a location where a heel of the user's hand would be, linkage 308 may attach to wearable base 302 at other locations, such as near the palm of the user or across a back of the user's hand. In any case, linkage 308 can extend from first end 312 to second end 314 to provide a mount for pivoted support 310 that locates center of rotation 316 at a spatial location that is comfortable for the user and within reach of the user's fingertips.

Linkage 308 can be disconnected from wearable base 302 and attached to another surface. In an embodiment, user console 120 includes a prong to receive first end 312 of linkage 308. For example, the receiving prong can extend from an armrest of user console, and thus, linkage 308 can be detached from wearable base 302 and attached to the armrest. Accordingly, detachable coupling 330 of linkage 308 can provide a quick connection to user console or wearable base 302. When linkage 308 is connected to user console 120, wearable base 302 may remain on the user's hand. The user may sit in user console 120 and manipulate the device component 200 that is supported by the armrest. When the UID 126 is docked on user console 120, the user can still experience many of the benefits of the wearable UID 126, including the ability to release the device component 200 without the risk that the device will be damaged by a fall.

Figure 4:
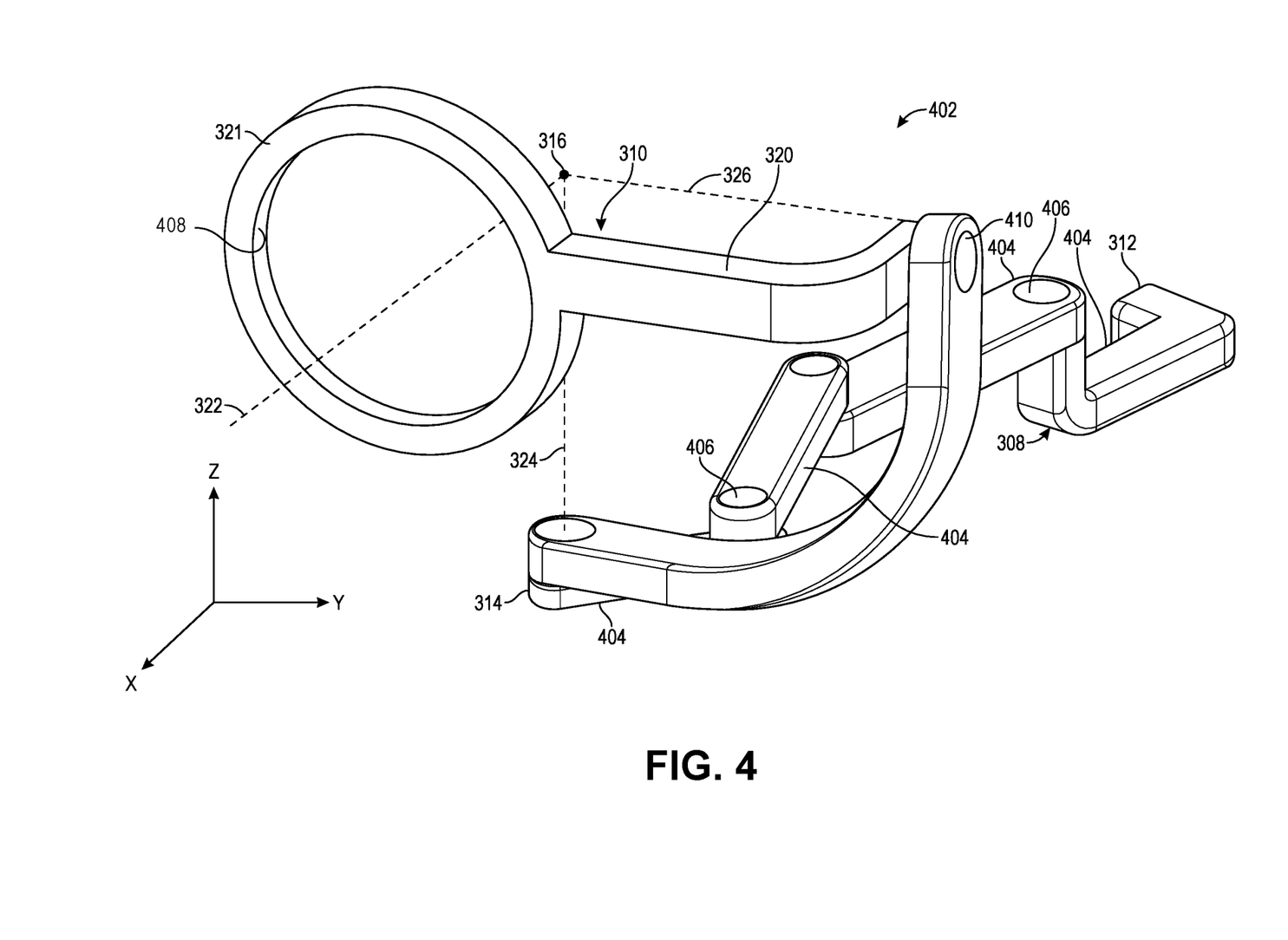
FIG. 4 is a perspective view of a support structure of a user interface device, in accordance with an embodiment.

Referring to FIG. 4, a perspective view of a support structure of a user interface device is shown in accordance with an embodiment. UID 126 can be provided as a unit having the trackable device component 200 connected to wearable base 302 by a support structure 402, e.g., linkage 308 and pivoted support 310, or portions of UID 126 can be separated as subunits. In an embodiment, support structure 402 is a subunit of UID 126. Similarly, wearable base 302 can be a subunit, and the device component 200 can be a subunit. The subunits may be separately combinable into a system with fewer components than the system shown in FIG. 3.

In an embodiment, support structure 402 includes linkage 308 and pivoted support 310. Linkage 308 can include one or more support members 404 that are interconnected. For example, support members 404 can be link arms coupled to each other via joints 406. Joints 406 can provide one or more degrees of freedom between first end 312 and second end 314 of linkage 308. By way of example, one or more of joints 406 may be revolute joints 406 that connect adjacent support members 404 and provide a degree of freedom of translation between first end 312 and second end 314. Joints 406 may be other types of joints 406, however. By way of example, one or more of joints 406 may be spherical joints 406 that connect adjacent support members 404 and provide several degrees of freedom of translation between first end 312 and second end 314. Alternative combinations of joints 406 include several revolute joints 406 having axes of rotation at different angles such that several degrees of freedom of translation are provided between first end 312 and second end 314. Accordingly, the interconnection between support members 404 allows second end 314 to move along one or more orthogonal axes relative to first end 312, e.g., along an x-axis, y-axis, or z-axis. The relative movement of the ends can be within a single plane, e.g., within an x-y plane containing x-axis and y-axis, and thus, linkage 308 can be referred to as a planar mechanism.

Pivoted support 310 can include respective joints 406 connecting the suspensions. For example, the device component (not shown) can be connected to roll suspension 321 via a first joint 408. First joint 408 can be a revolute joint formed between an inner surface of roll suspension 321 and an outer surface of the device component 200. For example, roll suspension 321 can be a collar having the inner surface surrounding the device component 200. Similarly, roll suspension 321 can be a roller bearing having an inner race mounted on the device component 200, and an outer race connected, e.g., fixed to, pitch suspension 320. In any case, device body 204 can rotate about roll axis 322 that extends through a center of roll suspension 321 and intersects with pitch axis 326 and yaw axis 324 at center of rotation 316.

Pivoted support 310 can include a gimbal set having two or more axes of rotation. In an embodiment, the gimbal set is a two-axis gimbal. The gimbal set can include pitch suspension 320, which is connected to yaw suspension 318 via a second joint 410. Pitch suspension 320 can rotate relative to yaw suspension 318 about pitch axis 326, which extends through second joint 410 and center of rotation 316. Similarly, yaw suspension 318 can be connected to second end 314 of linkage 308 at a corresponding joint. Yaw suspension 318 can rotate relative to second end 314 of linkage 308 about yaw axis 324, which extends through the corresponding joint and center of rotation 316. Accordingly, the gimbal set can include several suspensions connected by revolute joints having axes that intersect at center of rotation 316.

Figure 5:
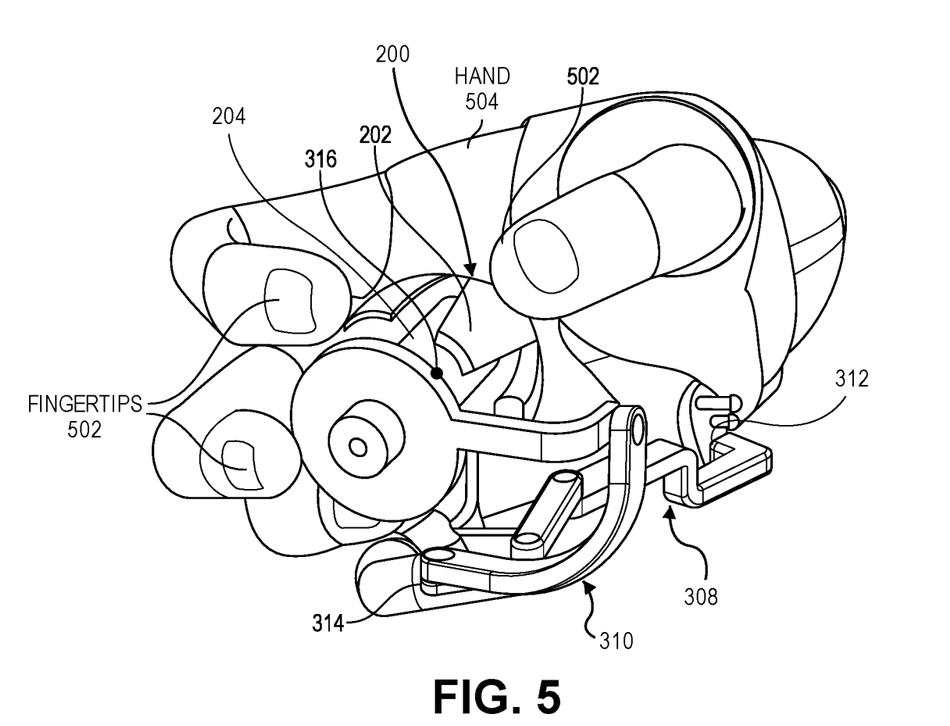
FIG. 5 is a perspective view of a user interface device worn on a user's hand, when the user interface device is being manipulated by the user's hand, in accordance with an embodiment.

Referring to FIG. 5, a perspective view of a user interface device worn on a user's hand when the user interface device is not manipulated by the user's hand is shown in accordance with an embodiment. In an embodiment, linkage 308 and pivoted support 310 can hold device body 204 at a position in space such that center of rotation 316 is located between the fingertips 502 of a hand 504 of the user. For example, second end 314 of linkage 308 can extend distally from first end 312 to position center of rotation 316 where the fingertips 502 can naturally hold the grip components 202. Linkage 308 and pivoted support 310 allows the user to manipulate device body 204 with full freedom. For example, by holding grip components 202 around center of rotation 316, the user can twist the device component 200 to rotate device body 204 about roll axis 322, tilt the device component 200 to rotate device body 204 about pitch axis 326, or sweep the device component 200 to rotate device body 204 about yaw axis 324. Such rotations are facilitated by articulation of pivoted support 310. The user can also translate device body 204 through translations by stretching or retracting her fingers, pivoting her wrist laterally or vertically, etc. Such translations are facilitated by articulations of linkage 308. Accordingly, fine finger manipulation of device body 204 can be performed with high dexterity.

By positioning center of rotation 316 at a middle of device body 204, the user may experience a more natural feeling when manipulating the device component 200. More particularly, maintaining the support structure 402 within the range of motion of the user's wrist and hand 504 can prevent singularities from occurring in the degrees of freedom of linkage 308 and pivoted support 310. When the user is manipulating UID 126, which is mounted on the user's wrist, the range of motion of the fingers does not allow any of the axes that establish a degree of freedom from aligning with another axis that establishes another degree of freedom. By way of example, a user cannot tilt device body 204 about pitch axis 326 far enough to align pitch axis 326 with yaw axis 324. Accordingly, the wearable UID 126 naturally reduces a likelihood and/or eliminates the possibility of a singularity occurring that can cause the linkage system to bind. Movement of the wearable UID 126 is therefore reliable and natural.

Manipulation of the device component 200 can be performed while keeping the hand 504 and arm in one stationary position and orientation. Alternatively, the user may move the arm and hand 504 to any position that is comfortable. Thus, the user fatigue can be reduced and user comfort can be increased. In addition to increasing comfort by improving mobility, the wearable UID 126 also allows the user to reduce fatigue by taking rests.

Figure 6:
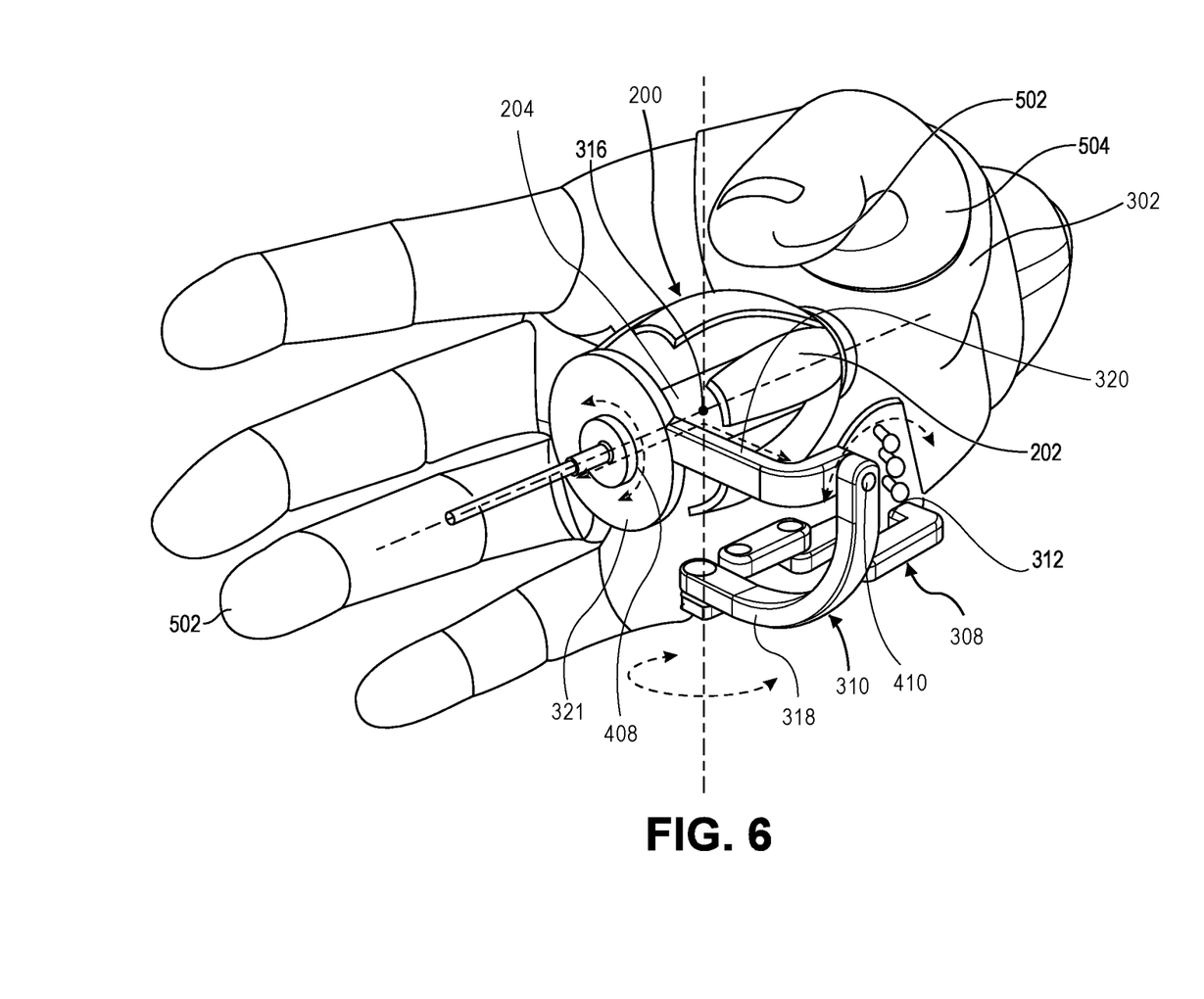
FIG. 6 is a perspective view of a user interface device worn on a user's hand, when the user interface device is not being manipulated by the user's hand, in accordance with an embodiment.

Referring to FIG. 6, a perspective view of a user interface device worn on a user's hand when the user interface device is not manipulated by the user's hand is shown in accordance with an embodiment. During usage, the user can take a short break by releasing grip components 202 and allowing device body 204 to remain suspended at center of rotation 316 within a range of grip of hand 504. More particularly, linkage 308 and pivoted support 310 can suspend device body 204 in a cantilevered fashioned from first end 312 of linkage 308. The user can then stretch her fingers while device body 204 remains in its relative position and orientation to hand 504. Notably, when the user releases the device component 200, the suspended device component 200 does not drop, and thus, the wearable UID 126 reduces a likelihood of damage to the device component 200 caused by accidental falls.

In addition to preventing drops, the wearable UID 126 can have a balanced design such that the device body 204 remains stationary at center of rotation 316 when the user releases the device component 200. More particularly, device body 204 and one or more components of support structure 402, e.g., linkage 308 or pivoted support 310, can maintain poses when UID 126 is not touched or manipulated by the user's hand 504 or fingers. In part, the balanced design can include the co-location of a center of mass of the device component 200 with center of rotation 316. Placing the center of mass coincident to center of rotation 316 can reduce the torque applied to the joints 406 of support structure 402 by the weight of the device component 200 when the device component 200 is not held by fingertips 502 of the user. When the applied torques are less than the natural resistance to motion of the support structure joints 406, the linkage system can be in a static state, and device body 204 may remain stationary about center of rotation 316.

As described above, joints 406 of support structure 402 can influence the stability of device body 204 when the user releases the device, e.g., to rest her fingers. More particularly, the stability of the support structure 402 is influenced by resistances to rotation of the joints 406. For example, first joint 408 connecting device body 204 to roll suspension 321 (and in turn to pitch suspension 320) can have a first resistance to rotation. Similarly, second joint 410 connecting pitch suspension 320 to yaw suspension 318 can have a second resistance to rotation. The resistances of rotation of each of the joints 406 of the linkage system can be set to be greater than an expected torque applied by the weight of the device component 200 when the user releases the device component 200. In an embodiment, the first resistance is less than the second resistance. For example, torque applied by the weight of the device component 200 may be greater at second joint 410 than at first joint 408, and accordingly, the resistances of the joints may decrease in the direction from second joint 410 to first joint 408. Similarly, a resistance to rotation of the joint 406 connecting yaw suspension 318 to linkage 308 may be greater than the second resistance. Accordingly, when the user releases the device component 200, an orientation of the device body 204 may remain constant relative to hand 504.

The stability of device body 204 can have several benefits. For example, maintaining device body 204 stationary upon release can reduce an amount of time required to re-align the orientation of device body 204 to surgical instrument 104 during engagement of the surgical robot 121. Similarly, the stability allows the user to release the device component 200 in a natural way and be mentally disengaged because the user can expect that the device body 204 will be in the same position and orientation when the user mentally re-engages and grasps grip components 202.

Another advantage of the balanced design of the linkage system is that it increases a range of motion of the device in the roll direction (about roll axis 322). When the user wants to rotate device body 204 about roll axis 322 more than the rotational range of the wrist of the user is capable of, the user can first rotate her hand to roll the device in a first rotational direction about roll axis 322. When the user reaches a limit of her natural wrist range, the user can release the device and rotate her hand back in a direction opposite to the first rotational direction. The user can then grasp the device and roll the device again in the first rotational direction. The grip/rotate/release cycle can be repeated until the device has been rolled to the desired rotational angle about roll axis 322. Accordingly, the support structure 402 can improve usability and rotational range of the wearable UID 126.

The joints 406 of the support structure 402 can be mechanically passive pivot joints, such as simple pin joints, as described and illustrated above. In an embodiment, one or more joints 406 of support structure 402 incorporate sensors, e.g., encoders, to detect a relative position between the components that the joints couple. Encoders may be included on each joint 406 of support structure 402 to determine pose. For example, an encoder in second joint 410 can detect a relative rotational angle about yaw axis 324 between an arm or ring of yaw suspension 318 and the distalmost support member 404 of linkage 308. When several of the joints 406 include encoders, the position information derived from the encoders can be used to determine an overall orientation of support structure 402. For example, by detecting an orientation of each joint 406 between first end 312 of linkage 308 and first joint 408 at roll suspension 321, the relative position and orientation of center of rotation 316 to first end 312 can be determined. Furthermore, the relative position between wearable base 302 and device body 204 (both rotational and translational) can be determined through the kinematics of the linkage system as described by the encoder information.

The position and orientation information derived from the encoders within the joints 406 can be combined with other tracking information to determine an overall spatial state of the wearable UID 126. For example, a tracking sensor can be incorporated in wearable base 302 instead of or in addition to tracking sensor 214 located within device body 204. The tracking sensor of wearable base 302 can be tracked optically, electromagnetically, etc., to determine a position in space of wearable base 302. When the location of the receiving prong on the wearable base 302 is known, the location information can be combined with position information derived from the joint sensors to determine an absolute location or orientation of center of rotation 316 in the workspace.

One or more joints 406 of support structure 402 may be flexures or compliant joints 406. For example, each support member 404 of linkage 308 may be connected to an adjacent support member 404 by an elastomeric flexure. The elastomeric flexure can deform to allow the support members 404 to move relative to each other. The flexure(s) can be compliant, such that when the deforming force is removed, e.g., when the user releases the device component 200, the flexure(s) can return linkage 308 to an initial, undeformed, state.

In an embodiment, one or more joints 406 of support structure 402 are motorized. The motors can be mounted on one or more of the joints 406 to impart a rotational force to one or more of the members of support structure 402. For example, a motor can be mounted at second joint 410 connecting pitch suspension 320 to yaw suspension 318. The motor can be controlled to impart the force for several reasons. The motor can move, vibrate, or otherwise drive pitch suspension 320 to deliver a haptic impulse to the user. Fingertips 502 are quite sensitive, and thus, the haptic impulse can be a relatively small force that can still be felt by the user. Accordingly, the motor can provide haptic feedback. The motor can also be used to hold a position of pitch suspension 320. For example, when the user releases the device component 200, the motors of support structure 402 can apply resistive torque to their respective joints 406 to counteract torques applied by the weight of the freely suspended device component 200. Accordingly, the motor can maintain device body 204 in a static state when the user releases the device component 200. In an embodiment, the motor can be used to avoid singularities within the mechanism. For example, although the wearable UID 126 inherently reduces a likelihood of a singularity occurring in pivoted support 310, if several axes of pivoted support 310 were to align, e.g., if pitch axis 326 aligned with yaw axis 324, the motor at second joint 410 can impart a force to break the alignment between the axes such that the singularity is avoided and the gimbal set continues to move smoothly.

Control signals input through UID 126 may be communicated to computer system 110 through a wired or wireless connection. In an embodiment, an electrical wire extends from a distal tip of UID 126, e.g., from distal end 210, to connect UID 126 to computer system 110. The electrical wire may provide power to UID 126 and may carry sensor signals, e.g., spatial state signals, grip signals, interlock off signals, clutch signals, etc., to computer system 110. Accordingly, UID 126 may be a peripheral device used to input commands to computer system 110. UID(s) 126 can be used in combination with other peripheral input devices. For example, a foot pedal switch may be connected to computer system 110 to provide a clutch input to surgical robotic system 100. Whereas each UID 126 may be individually clutched to pause teleoperation of respective surgical robotic arms 112 or graspers of respective surgical instruments 104, the respective surgical robotic arms 112 or surgical instruments 104 may be clutched at a same time by pressing the foot pedal switch. Thus, movement of actuators 114 may be manipulated by UIDs 126 and other peripheral input devices of computer system 110.

In an embodiment, tracking sensor 214 of UID 126 generates a spatial state signal, e.g., an input pose signal, representing movement of UID 126. The spatial state signal can be output to one or more processors communicatively coupled to UID 126 and coupled to the surgical instrument 104. The one or more processors can receive the spatial state signal from tracking sensor 214. The one or more processors can analyze or modify the signal, and output the resulting spatial state signal to user console 120. User console 120 may in turn control motions of surgical instrument 104 based on the tracked movements of UID 126.

In addition to tracking movement of UID 126 in space, movement of or pressure on one or more grip components 202 of UID 126 can be detected. For example, grip component 202 can include a grip linkage displacement sensor to generate a grip signal for manipulating a grip motion of the surgical instrument 104. The grip signal can represent movement of grip components 202 of UID 126. The grip linkage displacement sensor can detect motion or position of slider 220 relative to a reference point of device body 204, e.g., a proximal surface of device head 212. The detected position information can be output to the one or more processors. The one or more processors can detect, based on the received signal from the grip linkage displacement sensor, a movement of grip components 202 relative to device body 204 of UID 126. UID 126 can analyze or modify the signal, to generate and output the resulting grip signal to user console 120. User console 120 may in turn control motions of surgical instrument 104 based on the grip signal of UID 126.

UID 126 described above for use in a surgical procedure may be used in other applications. For example, UID 126 may be used in a virtual reality or augmented reality scenario. In such scenarios, UID 126 can be an input device that may be manipulated by a user to control an element being displayed to the user on a display device, e.g., a head-mounted display. The element may be a visual rendering of a surgical instrument, or any other element. For example, UID 126 can be used as a game controller to control an interaction between a user and a visual rendering of an object within an interactive gaming experience. Such applications are provided by way of example, and not limitation, and other applications are contemplated. For example, UID 126 can be used as an input device to control objects of various types. By way of example, UID 126 can be used to control drones, robots (such as pipe-cleaning robots), or other virtual or physical objects. One skilled in the art will therefore appreciate that UID 126 is described above largely in connection with robotic surgery, however, UID 126 is independent of such an application. That is, UID 126 can be used as an input device to provide input commands in many other applications that can be contemplated by one skilled in the art.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A user interface device for manipulating a surgical instrument in a surgical robotic system, comprising:
   a wearable base to be worn on a user's hand;
   a linkage having a first end mounted on the wearable base, and a second end;
   a pivoted support coupled to the second end of the linkage and including a plurality of suspensions having respective axes, wherein the respective axes are orthogonal to each other; and a device body mounted on the pivoted support such that the orthogonal axes intersect at a center of rotation located inside the device body.

2. The user interface device of claim 1, wherein the second end of the linkage extends from the first end such that the center of rotation is positioned at fingertips of the user's hand.

3. The user interface device of claim 2, wherein the linkage includes one or more support members coupled to each other via joints to provide one or more degrees of freedom of translation between the first end and the second end of the linkage.

4. The user interface device of claim 1, wherein the device body and the linkage maintain poses when the user interface device is not touched by fingertips of the user's hand.

5. The user interface device of claim 1, wherein the plurality of suspensions includes a roll suspension having a roll axis, a pitch suspension having a pitch axis, and a yaw suspension having a yaw axis, and wherein the device body is coupled to the roll suspension and the yaw suspension is coupled to the second end of the linkage.

6. The user interface device of claim 5, wherein the device body is coupled to the roll suspension via a first joint, and wherein the pitch suspension is coupled to the yaw suspension via a second joint.

7. The user interface device of claim 6, wherein a first resistance to rotation of the first joint is less than a second resistance to rotation of the second joint.

8. The user interface device of claim 1, wherein the wearable base includes one or more of a wrist piece or a hand piece to be worn around the user's hand.

9. The user interface device of claim 1, wherein the linkage is coupled to the wearable base at the first end by a detachable coupling.

10. The user interface device of claim 1 further comprising a plurality of grip components pivotally coupled to the device body, wherein the grip components are configured to generate a grip signal for manipulating a grip motion of the surgical instrument.

11. A user console for manipulating a surgical instrument in a surgical robotic system, comprising:
a user interface device including
a wearable base including one or more of a wrist piece or a hand piece to be worn around a hand of a user,
a linkage having a first end mounted on the wearable base, and a second end,
a pivoted support coupled to the second end of the linkage and including a plurality of suspensions having respective axes, wherein the respective axes are orthogonal to each other, and
a device body mounted on the pivoted support such that the orthogonal axes intersect at a center of rotations located inside the device body; and
a tracking system configured to track movements of the user interface device and to generate signals to control motions of the surgical instrument.

12. The user console of claim 11, wherein the second end of the linkage extends from the first end such that the center of rotation is positioned at fingertips of the user's hand.

13. The user console of claim 12, wherein the linkage includes one or more support members coupled to each other via joints to provide one or more degrees of freedom of translation between the first end and the second end of the linkage.

14. The user console of claim 11, wherein the device body and the linkage maintain poses when the user interface device is not touched by fingertips of the user's hand.

15. The user console of claim 11, wherein the plurality of suspensions include a roll suspension having the roll axis, a pitch suspension having the pitch axis, and a yaw suspension having the yaw axis, and wherein the device body is coupled to the roll suspension and the yaw suspension is coupled to the second end of the linkage.

16. The user console of claim 15, wherein the device body is coupled to the roll suspension via a first joint, and wherein the pitch suspension is coupled to the yaw suspension via a second joint.

17. The user console of claim 16, wherein a first resistance to rotation of the first joint is less than a second resistance to rotation of the second joint.

18. A surgical robotic system, comprising:
a surgical instrument mounted on a surgical robotic arm;
a user interface device including
a wearable base to be worn on a user's hand,
a linkage having a first end mounted on the wearable base, and a second end,
a pivoted support coupled to the second end of the linkage and including a plurality of suspensions having respective axes, wherein the respective axes are orthogonal to each other, and
a device body mounted on the pivoted support such that the orthogonal axes intersect at a center of rotation located inside the device body; and
one or more processors communicatively coupled to the user interface device and the surgical instrument and configured to control motions of the surgical instrument based on tracked movements of the user interface device.

19. The surgical robotic system of claim 18, wherein the second end of the linkage extends from the first end such that the center of rotation is positioned at fingertips of the user's hand.

20. The surgical robotic system of claim 18, wherein the device body and the linkage maintain poses when the user interface device is not touched by fingertips of the user's hand.

* * * * *